US006476596B1

(12) United States Patent
Wraback et al.

(10) Patent No.: US 6,476,596 B1
(45) Date of Patent: Nov. 5, 2002

(54) METHOD AND APPARATUS FOR DETECTION OF TERAHERTZ ELECTRIC FIELDS USING POLARIZATION-SENSITIVE EXCITONIC ELECTROABSORPTION

(75) Inventors: Michael Wraback, Germantown, MD (US); Paul Shen, Potomac, MD (US); Mitra Dutta, Raleigh, NC (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/459,386

(22) Filed: Dec. 6, 1999

(51) Int. Cl.⁷ .............................................. G01R 31/02
(52) U.S. Cl. .................................. 324/158.1; 250/338.4
(58) Field of Search ................................ 324/96, 158.1, 324/97; 250/338.1, 458.1, 338.4; 257/21, 18; 375/37; 359/248

(56) References Cited

U.S. PATENT DOCUMENTS

| 5,056,111 A | * | 10/1991 | Duling et al. ................. 375/37 |
| 5,272,356 A | * | 12/1993 | Wen et al. ..................... 257/21 |
| 5,293,213 A | * | 3/1994 | Klein et al. ................. 250/458.1 |
| 5,313,073 A | * | 5/1994 | Kuroda et al. ................. 257/18 |
| 5,381,260 A | * | 1/1995 | Ballato et al. .............. 359/248 |
| 5,488,226 A | * | 1/1996 | Iafrate et al. ............ 250/338.4 |
| 5,748,359 A | * | 5/1998 | Shen et al. ................. 359/248 |
| 5,789,750 A | * | 8/1998 | Nuss ....................... 250/338.1 |
| 5,914,497 A | * | 6/1999 | Sherwin ...................... 257/21 |
| 6,078,047 A | * | 6/2000 | Mittleman et al. ........ 250/338.1 |

FOREIGN PATENT DOCUMENTS

EP         0-606776 A2 *   7/1994    ........... H01L/31/09

* cited by examiner

*Primary Examiner*—Michael Sherry
*Assistant Examiner*—Jimmy Nguyen
(74) *Attorney, Agent, or Firm*—Paul S. Clohan, Jr.; Mark D. Kelly; Edward L. Stolarun

(57) ABSTRACT

A terahertz electromagnetic energy detector comprises a (100) oriented multiple quantum well thermally bonded to a first transparent substrate having a direction dependent thermal coefficient of expansion such that this coefficient matches the thermal coefficient of expansion of MQW in one direction but different form the direction-dependent thermal coefficient of expansion of the MQW in a perpendicular direction. The resultant internal thermally induced anisotropic strain leads to a polarization dependence of the optical absorption that is strongest near the lowest heavy-hole and light-hole exciton peaks. A second transparent substrate is placed beneath the first transparent substrate and is oriented so that its thermal coefficients of expansion act in a direction perpendicular to those of the first transparent substrate so that the accumulated phase retardation of the optical wave associated with birefringence of the substrate is effectively cancelled. A transverse electric and electromagnetic field is applied across the plane of the quantum well layers to ionize the excitons, which produces an anisotropic bleaching and concomitant line broadening of the anisotropic excitonic absorption. This phenomenon results in a polarization rotation of the transmitted optical field such that light passing through the device may be detected by a photosensitive polarization detector. The device is capable of effectively measuring the phase and frequency of terahertz energy over a wide bandwidth.

3 Claims, 10 Drawing Sheets

NO ANISOTROPIC STRAIN

ANISOTROPIC STRAIN →

ABSORPTION IN A 50 PERIOD MQW WITH 100Å GaAs WELLS AND 100Å $Al_{0.3}Ga_{0.7}As$ BARRIERS UNDER A ~ 0.2% COMPRESSIVE STRAIN PRIMARILY IN THE X-DIRECTION.

METHOD AND APPARATUS FOR DETECTION OF TERAHERTZ ELECTRIC FIELDS USING POLARIZATION-SENSITIVE EXCITONIC ELECTROABSORPTION

BACKGROUND OF THE INVENTION

Today's soldier is confronted with the possibility of coming in contact with deadly, invisible chemical or biological weapons of mass destruction. Lethal concentrations of biological weapons, in particular, are so minute that advance detection has been nearly impossible, particularly on the battlefield. In theory, any airborne substance, including chemical and biological warfare agents, can be detected by interrogation with terahertz electromagnetic waves. Accurate identification of substances by this method, however, requires precise measurement over a wide bandwidth of the amplitude and phase of the energy emitted from the interrogated object. To date, there have been no practical, high-sensitivity, broadband, terahertz detectors capable of detecting the amplitude and phase of terahertz electromagnetic waves. The present invention provides remarkably high sensitivity, ultra-wide bandwidth optical detection of both the amplitude and phase of a terahertz frequency or below electric field, and will enable detection in the field of trace amounts of chemical and biological warfare agents. The invention has numerous other civilian and military applications, including ultra-wide bandwidth wireless communication, optical sampling of submillimeter wave signals for optical A-D conversion, covert communications, and measurement of nonequilibrium transport in optoelectronic devices.

The invention will enable one to use the polarization properties of incident light to achieve higher sensitivity through background-free or polarization-sensitive detection. It is capable of better sensitivity than a conventional multiple quantum well detector which is hampered by the small amplitude modulation depth of the excitonic electroabsorption super-imposed upon a background of transmitted near-infrared light. Moreover, because the response time of the excitonic electroabsorption is only limited by the inverse of the exciton linewidth in the presence of the applied electric field, the invention also possesses wider bandwidth than other high sensitivity detectors such as photoconductive dipole antennas, the bandwidth of which is limited by the photogenerated carriers in the photoconductor.

BACKGROUND OF RELATED ART

Figure 1:
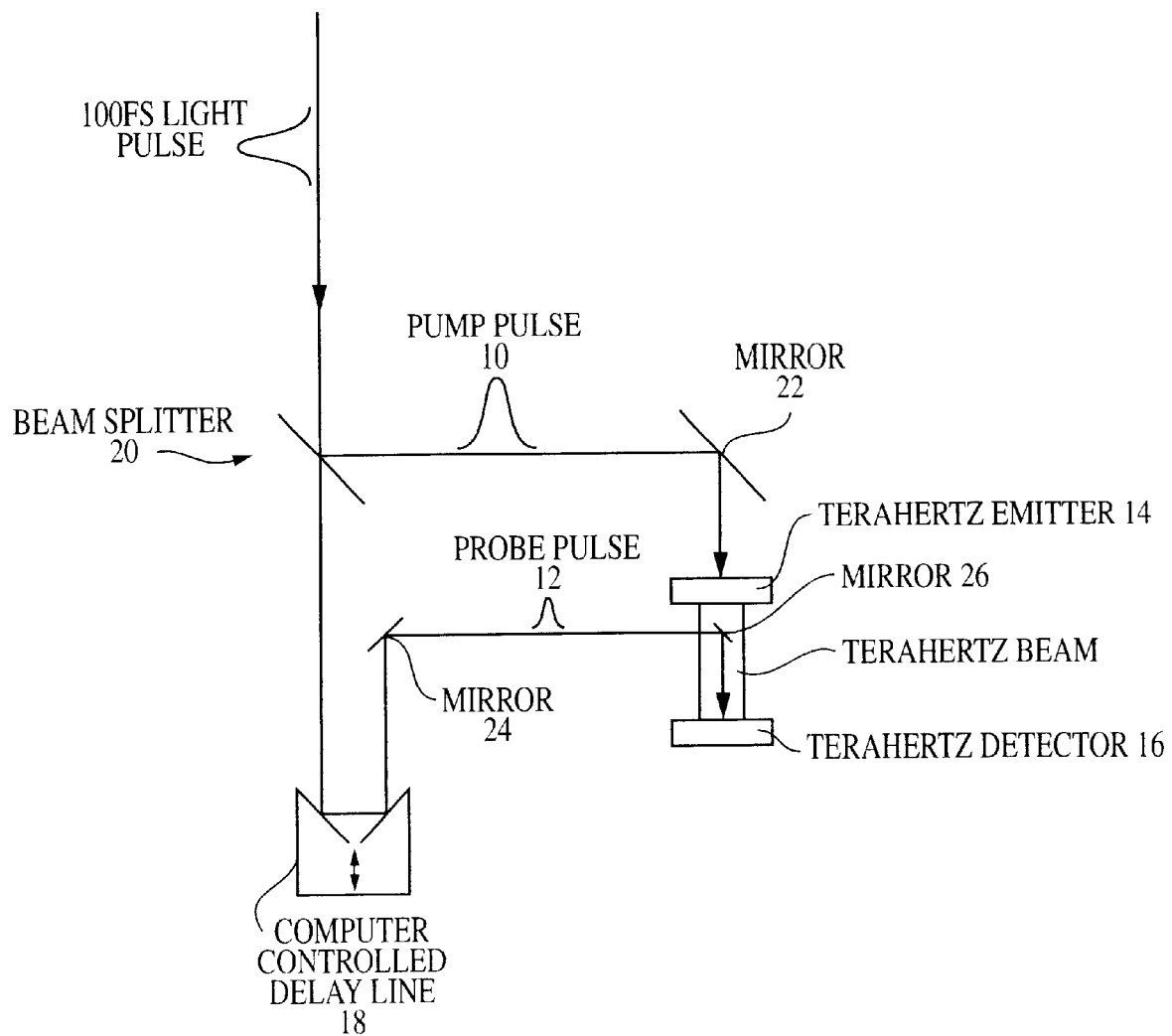
FIG. 1 shows a schematic representation of a system for use in connection with a terahertz electromagnetic detector.
Figure 2:
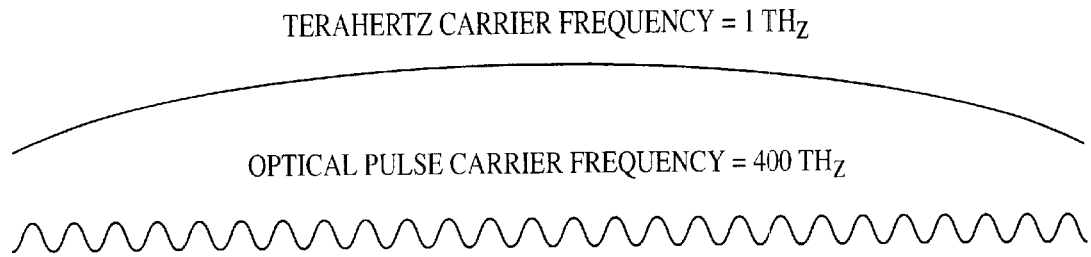
FIG. 2 shows a graph of the relationship between a terahertz carrier frequency and an optical pulse carrier frequency.

There are three basic ways in which terahertz electromagnetic detection has been performed in the past. Referring to FIG. 1, an excitation light pulse of approximately 100 femtoseconds is split into two pulses by beam splitter 20. One pulse is used to generate pump pulse 10, a broadband electromagnetic pulse with center frequency in the terahertz range. Pump pulse 10 is generated by either optical rectification at a semiconductor surface such as terahertz emitter 14, or by photoconductive switching (not illustrated). The other pulse, probe pulse 12, passes through computer controlled delay line 18 and is directed by mirrors 24 and 26 into terahertz detector 16. The details of the pulse generation would be familiar to those of ordinary skill in the art. What is important to note is that the broadband terahertz electromagnetic pulse is synchronized with both the excitation pulse and probe pulse 12. Since the femtosecond probe pulse 12 is much shorter in duration than the terahertz electromagnetic pump pulse 10 and the optical frequency of probe pulse 12 is such that many cycles at this frequency fit into one cycle of pump pulse 10, probe pulse 12 can sample a small portion of the waveform of pump pulse 10. In effect, the terahertz electromagnetic pump pulse 10 appears to probe pulse 12 as a static electric field as shown in FIG. 2. Because the electromagnetic pulse 10 and the probe pulse 12 are both derived from the excitation pulse, they are coherent with one another.

Figure 3:
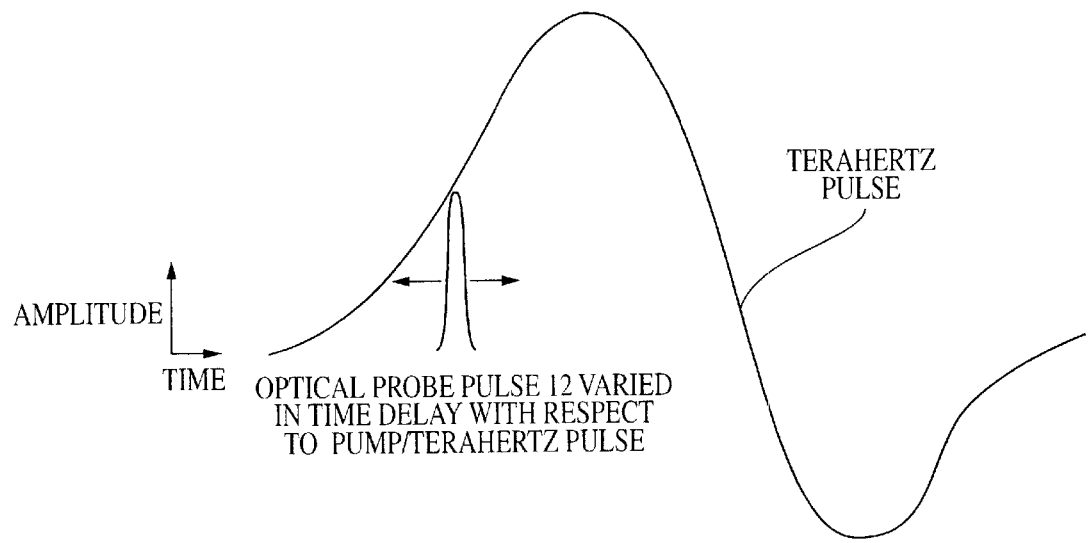
FIG. 3 shows a graph of the interrogation of a terahertz pulse by an optical probe pulse.

It is therefore possible to detect both the amplitude and phase of the electromagnetic pulse 10 by varying the time delay between the excitation and probe pulses with a variable delay line such as computer controlled delay line 18 such that the probe pulse samples many points along the electromagnetic pulse waveform as shown in FIG. 3.

Figure 4:
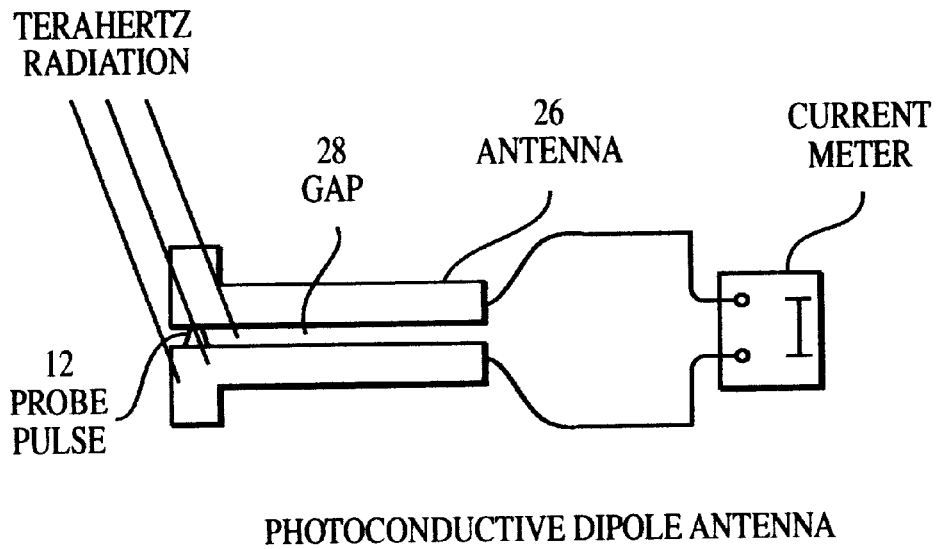
FIG. 4 shows a schematic representation of a photoconductive dipole antenna terahertz detector.

In order for detection to occur, the portion of the electromagnetic pulse being sampled must somehow modify the femtosecond probe pulse or the current produced by this optical pulse. The first method of detection {1} is by using an antenna with a gap on a semiconductor as shown in FIG. 4. When the electromagnetic pulse is incident on the antenna, it can generate a current if the gap is somehow closed. The gap may be closed by the femtosecond probe pulse 12, which creates electron-hole pairs through photoexcitation of electrons across the bandgap of the semiconductor. These carriers make gap 28 in antenna 26 conducting such that a current flows through the circuit when the electromagnetic pulse is incident on the antenna. This current will continue until the photoexcited carriers recombine and the gap is no longer conducting. The time scale of this recombination can be made much shorter than the duration of the electromagnetic pulse so that sampling becomes viable.

Figure 5:
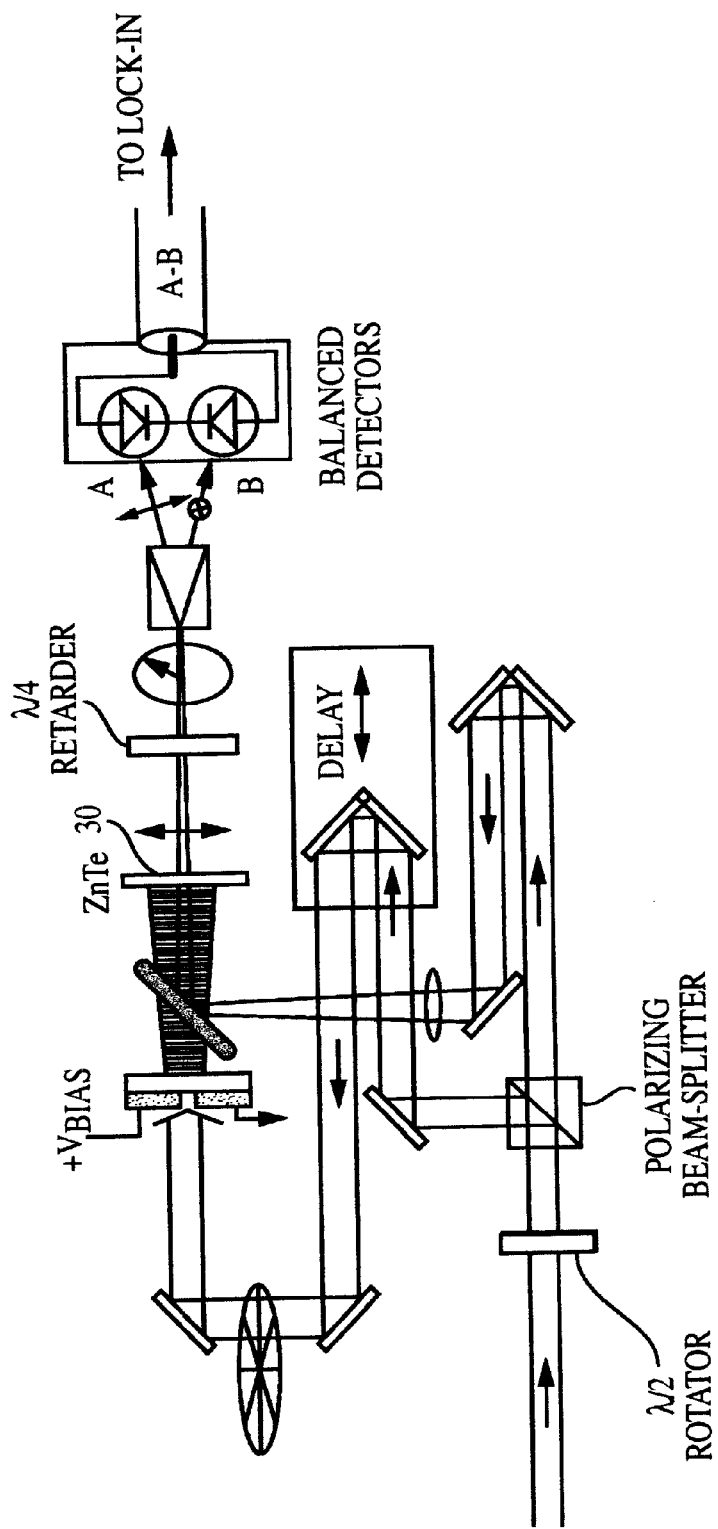
FIG. 5 shows a schematic representation of a terahertz detector exploiting the electro-optic effect in bulk ZnTe crystals.

The second method of detection, illustrated in FIG. 5, involves the electro-optic effect in bulk ZnTe crystals {2} grown normal to the (110) plane of the ZnTe crystal. These crystals have a birefringence, which is sensitive to the presence of the transverse electric field in an electromagnetic pulse propagating normal to the surface of the crystal. In the absence of the electromagnetic pulse, the femtosecond probe pulse is circularly polarized after passing through the detector such that it may be split into two equal parts by a polarizer and focused on to two equivalent photodiodes. The photocurrent from these diodes is subtracted to yield a null result. However, the transverse electric field in the electromagnetic pulse alters the birefringence of the ZnTe crystal such that the femtosecond probe pulse is no longer circularly polarized and the detectors no longer balance. In this way, manipulation of the polarization properties of the femtosecond probe pulse allows for very sensitive detection of the electric field of the sampled electromagnetic pulse.

Figure 6:
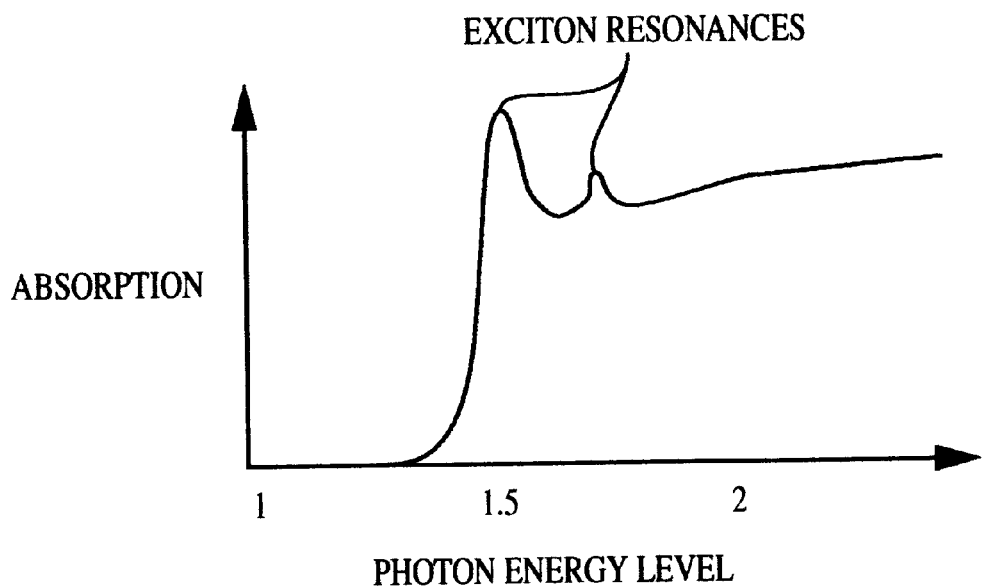
FIG. 6 shows a graph of exciton resonance peaks occurring in the photon energy absorption spectra of semiconductor.
Figure 7:
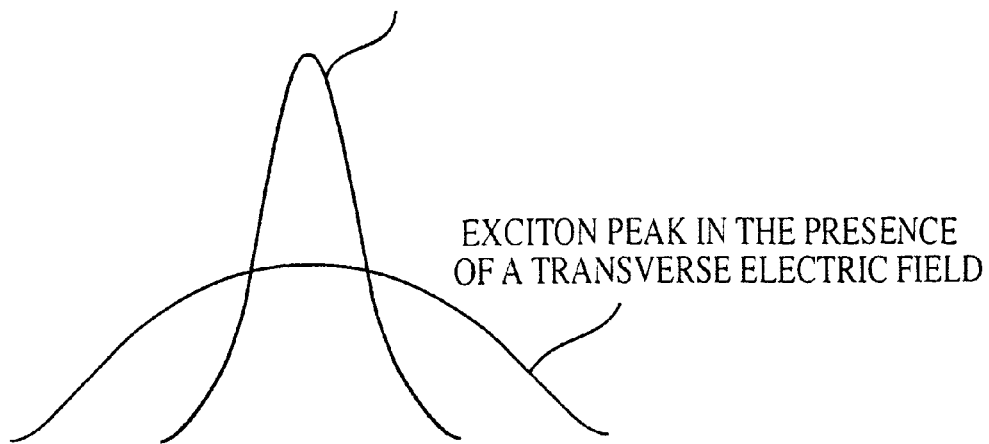
FIG. 7 shows a graph of an exciton peak with no electric field compared with an exciton peak in the presence of a transverse electric field.

The third method of detection involves using excitonic electroabsorption in a semiconductor multiple quantum well (MQW) {3}. An exciton is a superposition of single particle states representing the lowest excited state in a semiconductor. It corresponds to the photo-excitation of an electron such that the electron does not possess sufficient energy to escape from the Coulomb attraction of the hole it left behind. One can therefore think of the electron-hole pair in such a state as analogous to a mini hydrogen atom. The Coulomb attraction increases the overlap of the electron and hole wavefunctions such that an enhancement in absorption of photons occurs at the photon energy corresponding to exciton formation. Thus, the probability of absorbing a photon to create an exciton is higher than the probability of absorbing a photon to create a free electron-hole pair. This phenomenon manifests itself as a peak in the absorption spectrum of the semiconductor referred to as the exciton peak or resonance (FIG. 6). In a quantum well the effect of confinement in one direction is to increase the binding energy such that it is difficult for phonons associated with lattice vibrations to ionize the exciton at room temperature. Hence multiple quantum wells are useful for many optoelectronic devices because they have well-defined absorption peaks at room temperature. When an electric field is applied perpendicular to the direction of quantum confinement, the electron and hole are pulled apart, or ionized by this field. This leads to a bleaching and concomitant broadening of the exciton peak due to decrease in the exciton lifetime (FIG. 7). At low fields (less than 10 kV/cm) the increase in transmission is a nonlinear function of applied electric field, but at higher fields the behavior is quite linear. This implies that the detector must be biased at −10 kV/cm. The transverse electric field of the electromagnetic pulse then appears to the detector as a static electric field that causes a linear change in the transmission of the femtosecond pulse sampling the waveform. For further background the reader is directed to {1} J. T. Darrow, X.-C. Zhang, and D. H. Auston, *Appl. Phys. Lett.* 58, 25 (1991); {2} Q. Wu, M. Litz, and X.-C. Zhang, *Appl. Phys. Lett.* 68, 2924 (1996); {3} W. Sha, T. B. Norris, J. W. Burin, D. Woodard, and W. J. Schaff, *Appl. Phys. Lett.* 61, 1763 (1992), incorporated herein by reference.

Each of the above-described detectors suffers from various drawbacks. The first detector (dipole antenna) is limited by the finite time for the current to move in the gap and the lifetime of the photo-excited electrons and holes. Thus, it is not a sampling technique in which the sampling is instantaneous, thus requiring a deconvolution of the detector response from the sampled waveform. The second detector (ZnTe) is limited in that the electro-optic response is small for photons with energy much smaller than the bandgap of the material. This implies that a long interaction length (~1 mm) is necessary for uncomplicated use of the detector. Because of phase matching considerations between the electromagnetic pulse and the femtosecond probe pulse, the long interaction length indicates that there is only a small range of photon wavelengths around 800 nm at which sampling can be accomplished without necessitating deconvolution due to dispersion in the detector. The third detector, the multiple quantum well electroabsorption detector, operates on resonance so the interaction length is very small (~1 micron), but because it is not polarization sensitive, the sensitivity is lower than the ZnTe detector.

OBJECTS AND SUMMARY OF INVENTION

These and other shortcomings are overcome, at least in part, by the invention of the present application which includes a light polarization sensitive detector of terahertz frequency electromagnetic radiation having a multiple quantum well and having a top and a bottom, a first transparent substrate having a front and a back side, the front side of the first transparent substrate bonded to the bottom of the multiple quantum well, and having an anisotropy in the thermal coefficient of expansion in a plane substantially perpendicular to the surface normal of the multiple quantum well, a second transparent substrate substantially identical to the first transparent substrate positioned beneath the back side of the first transparent substrate and oriented such that an optical anisotropy of the first transparent substrate is offset by the second substrate; and metal contacts affixed to the top of the multiple quantum well. In a preferred embodiment, the transparent substrates of the light polarization sensitive detector of terahertz frequency electromagnetic radiation include LiTaO3 and the bond between the first transparent substrate and multiple quantum well is a high temperature thermal bond. The high temperature bond may be effected by using a UV-adhesive and a UV lamp.

Another aspect of the invention of this application includes a light polarization sensitive method of detecting terahertz frequency electromagnetic radiation including: modifying a multiple quantum well detector of terahertz energy to effect a thermally induced anisotropic strain of the multiple quantum well in a plane substantially perpendicular to the surface normal of the multiple quantum well, and operating the multiple quantum well detector of terahertz energy near an exciton resonance based on an anisotropic bleaching and concomitant line broadening of an anisotropic excitonic absorption by a transverse electric field.

Still other objects of the present invention will become readily apparent to those skilled in this art from the following description wherein, where there is shown and described a preferred embodiment of this invention, simply by way of illustration one of the modes to best carry out the invention. As it will be realized, the invention is capable of other different embodiments and its several details are capable of modification in various, obvious aspects all without departing from the invention. Accordingly, the drawings and descriptions will be regarded as illustrative in nature and not restrictive.

DETAILED DESCRIPTION

Figure 8:
FIG. 8 illustrates the effect of in-plane anisotropic strain on a crystal lattice.
Figure 8:
Figure 8:
Figure 8:
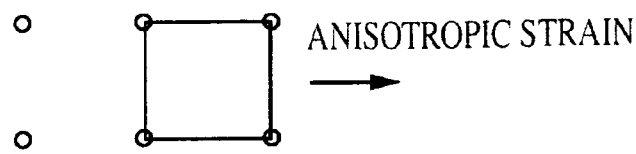
Figure 8:
Figure 9:
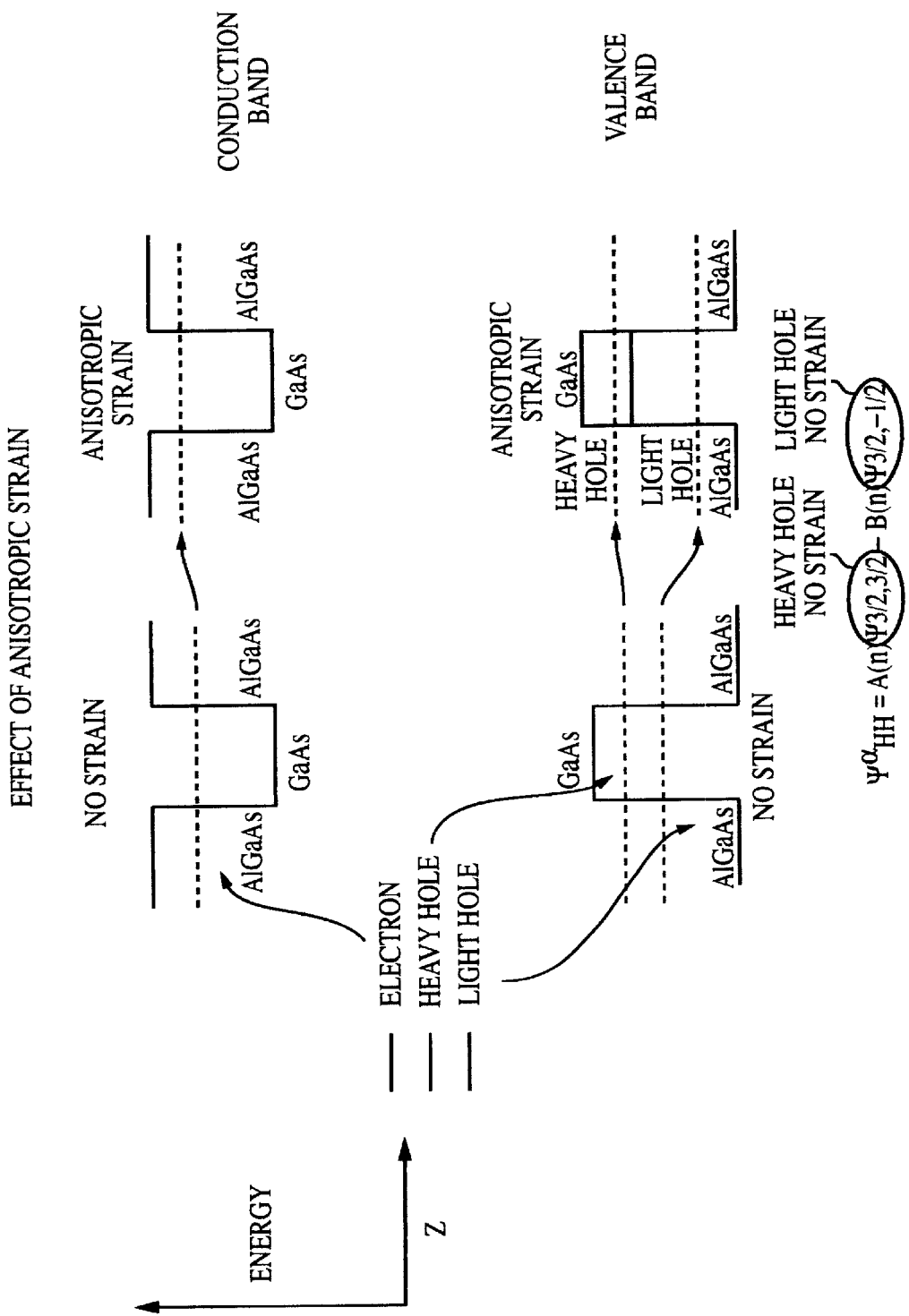
FIG. 9 shows the effect of anisotropic strain on electron and exciton energy band diagrams.
Figure 10:
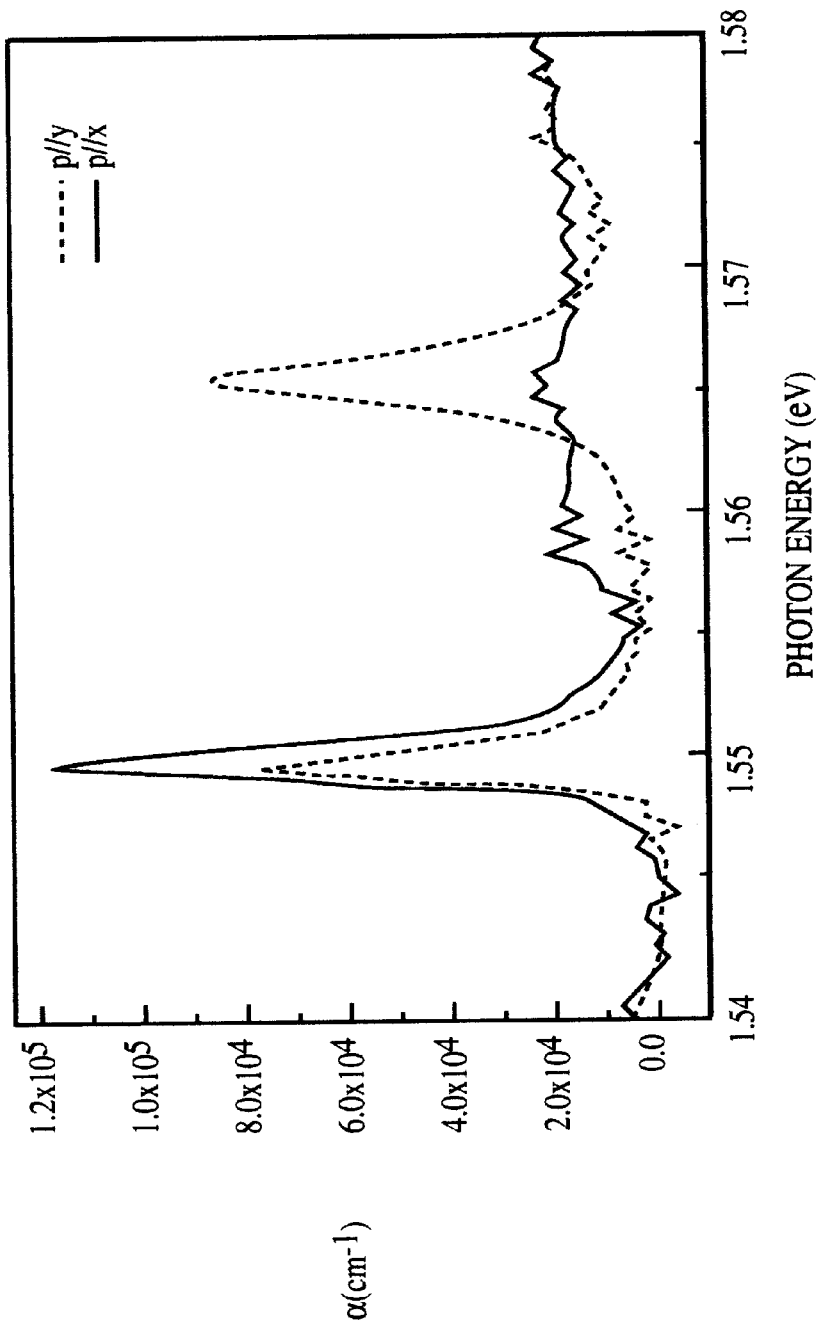
FIG. 10 shows a graph of the absorption anisotropy for a compressive anisotropic strain primarily along the x-direction in a multiple quantum well.

In-plane anisotropic strain means that, if one is looking along the surface normal of a material, the lattice constant in one direction is different from that in a perpendicular direction (FIG. 8). This is akin to saying that if one initially has a square, anisotropic strain will turn it into a rectangle. A square has four-fold rotation symmetry. This means that, when viewed along the surface normal, a rotation about an axis parallel to the surface normal through an angle of 90 degrees will leave the square unchanged. There are four such rotations possible within 360 degrees. Hence, we speak of fourfold rotation symmetry. It is clear that a rectangle, according to the above discussion, would have only two-fold rotation symmetry. Therefore the introduction of anisotropic strain leads to a lowering of rotation symmetry when viewed along the surface normal. With regard to a crystal lattice, we know from quantum mechanics that such a lowering of symmetry leads to a mixing of the wave functions of different valence bands near the Brillouin Zone center (crystal momentum k=0). In the absence of anisotropic strain, there are certain wave functions along the <100> directions (surface normal) that correspond to good quantum numbers, or stationary states, of the material. One of these would be energy. When a system is in a stationary state of energy, any measurement of the energy of that state will always give the same result. However, when one introduces an anisotropic strain, the symmetry of the material is changed, and the wave functions of the previous stationary states no longer possess good quantum numbers for the strained material. One must therefore construct new stationary states comprised of components of the previous stationary states. This is what is meant by mixing of the valence band wave functions, shown in FIG. 9. In a quantum well, the lowest valence bands participating in the mixing are the heavy-hole and light-hole valence bands, so named because the curvature of the bands is such that the mass of holes is larger for the former than for the latter. This mixing of the valence band wave functions leads to an anisotropy in the optical absorption as well as birefringence, most prevalent at photon energies corresponding to the creation of either heavyhole-like (transitions between the heavy-hole-like and conduction bands) or light-hole-like (transitions between the light-hole-like and conduction bands) excitons. The absorption anisotropy for a compressive anisotropic strain primarily along the x-direction is characterized by enhanced absorption at the heavy-hole-like exciton resonance for light polarized parallel to the strain direction, and diminished absorption for light polarized perpendicular to the strain axis. This trend is reversed at the light-hole-like exciton resonance, at which light polarized perpendicular to the strain axis is more strongly absorbed than its orthogonal counterpart as illustrated in FIG. 10. These descriptions are reversed for tensile anisotropic strain. In all of these cases the Krainers-Kronig relations govern the spectral dependence of the associated strain-induced birefringence.

Figure 11:
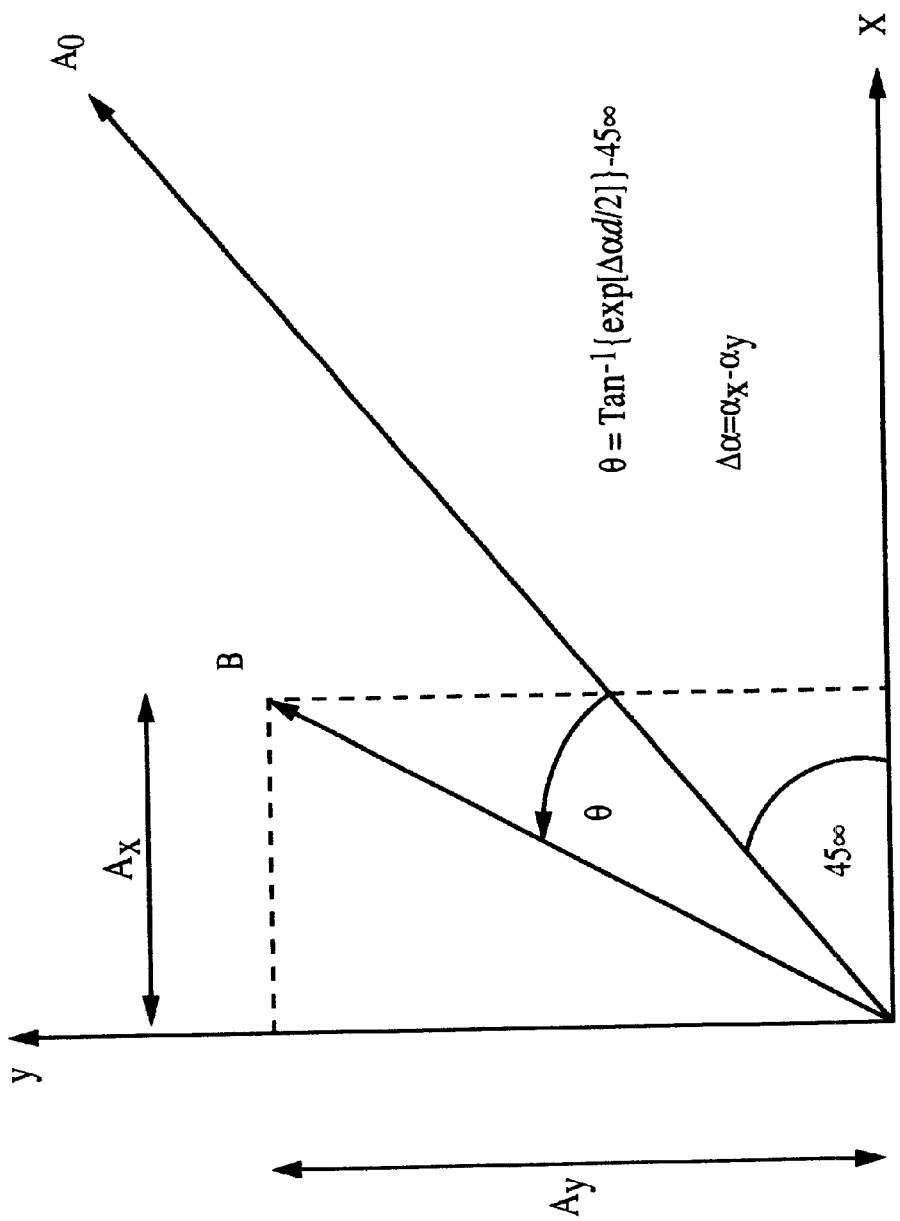
FIG. 11 shows a graph of the light intensity of light emitted from a multiple quantum well in the absence of anisotropic strain compared with light emitted from a multiple quantum well in the presence of anisotropic strain.
Figure 12:
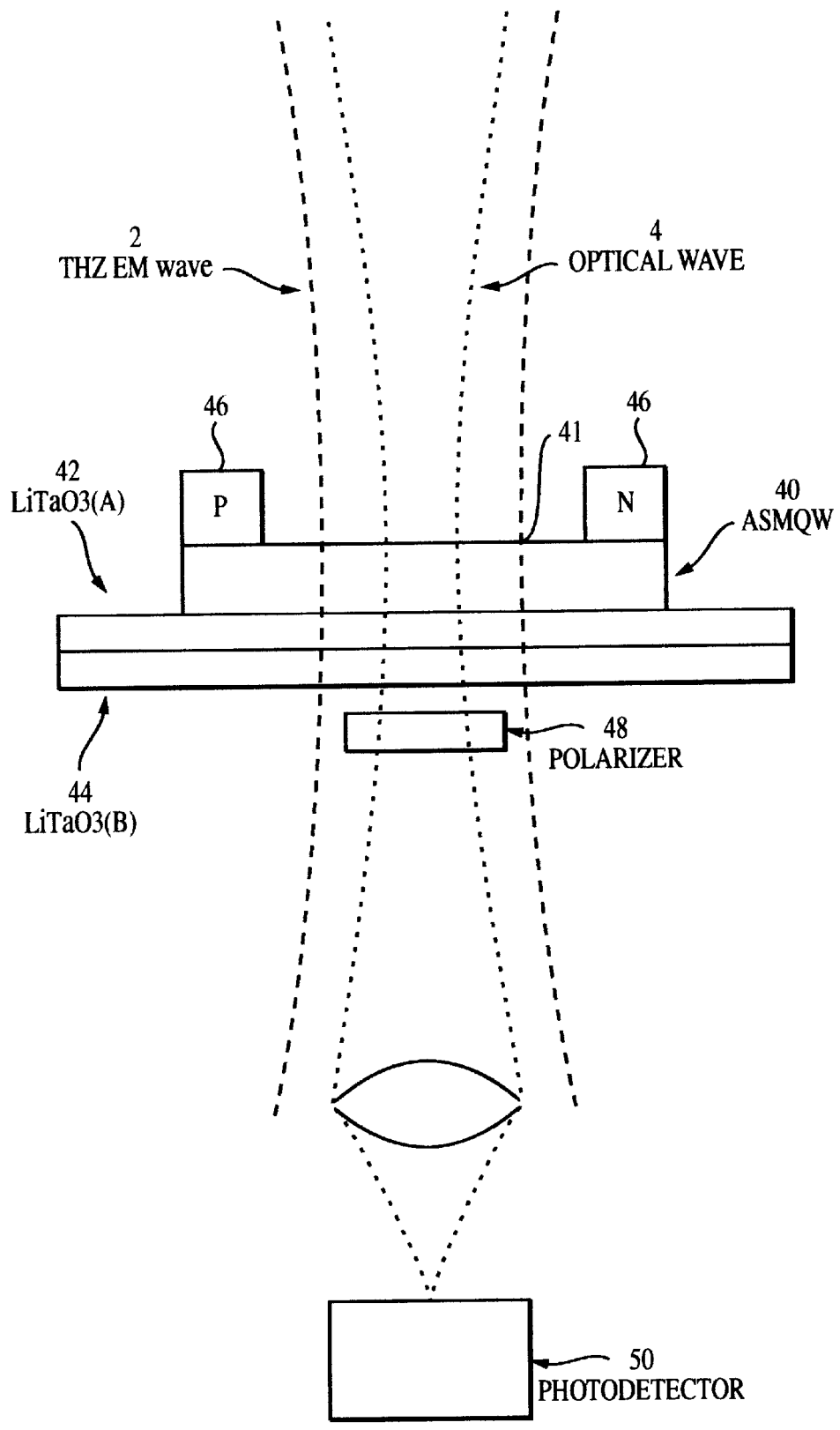
FIG. 12 shows a preferred embodiment of a terahertz detector.

Focusing on the heavy-hole-like exciton resonance, consider a case in which the light incident on the MQW is polarized at 45 degrees with respect to the x-axis. In the absence of anisotropic strain, the components of the light with polarization along the x- and y-directions would be absorbed equally, and the resultant light would still be polarized at 45 degrees with respect to the x-axis. However, in the presence of compressive anisotropic strain primarily along the x-direction, the component of the light with polarization along the x-direction is absorbed more strongly at the heavy-hole-like exciton resonance than the y-polarized component, thus leading to a polarization rotation of the emergent light toward the y-axis illustrated in FIG. 11. This is only one example of how the material has now become sensitive to the polarization state of the incident light. At other photon energies the light may experience both polarization rotation and phase retardation, depending on the absorption anisotropy and the strain-induced birefringence. The anisotropic strain must be internal to the device as shown in FIG. 12. One way in which such a strain may be created is by bonding the MQW at high temperature to a transparent substrate with a direction- dependent thermal expansion coefficient. Upon cooling to room temperature the device will possess an internal anisotropic strain. The substrate most often used is lithium tantalate (LiTaO3.). One way in which the bonding may be effected is by using a UV-adhesive and a UV lamp. The new substrate also adds a static birefringence to the device which must be cancelled. This may be done by attaching a second identical substrate oriented perpendicular to the host substrate, or by providing some other means of external phase compensation. Metallic contacts attached to the surface of the MQW are used to apply a static electric field parallel to the surface of the device, as discussed above for the electroabsorption detector. In order for these metallic contacts to be attached, the growth substrate must be removed from the MQW (top of the device). This process is often effected by etching. The device subsequently functions as a polarization-sensitive electroabsorption detector. The transverse electric field of the incident terahertz frequency EM wave causes an anisotropic bleaching of the lowest heavy-hole-like exciton resonance associated with the field-induced ionization of the probe-created excitons. For probe light initially polarized at 45 degrees with respect to the strain axis of the sample, this phenomenon causes a polarization rotation and/or phase retardation of the probe light passing through the detector. Polarization-sensitive detection may be achieved by either using a polarizer crossed with respect to the transmitted light in the absence of the sub-mm EM wave, or a beamsplitter and two detectors whose output is balanced in the absence of the EM wave.

If the source of the EM wave is synchronized with that of the probe pulse, then the probe pulse can sample many points in the EM wave form with resolution given by the probe pulse width. Thus, the entire EM waveform can be mapped out by varying the time delay between the probe pulse and the EM wave and the substance under inspection can be characterized simply and effectively.

FIG. 12 shows a preferred embodiment of the terahertz polarization-sensitive detector of this application. A multiple quantum well (MQW) 40 is grown on a (100) oriented flat substrate. The substrate/MQW structure 40 should be of sufficient size to permit the passage of an electromagnetic wave 2 in the terahertz frequency range or below through a transmission window 41 located in the center of MQW 40 and to allow for placement of metal contacts 46 on either side of transmission window 41 in MQW 40. MQW 40 is bonded to a transparent substrate 42 at elevated temperature. Substrate 42 has a direction dependent thermal coefficient of expansion such that this coefficient matches the thermal coefficient of expansion of MQW 40 in one direction but is significantly different form the direction-dependent thermal coefficient of expansion of MQW 40 in a perpendicular direction. Cooling of this structure to room temperature results in an internal thermally induced anisotropic strain. This strain leads to a polarization dependence of the optical absorption that is strongest near the lowest heavy-hole and light-hole exciton peaks. A second transparent substrate 44 having an identical direction-dependent thermal coefficient of expansion is placed beneath the first transparent substrate 42 and is oriented so that its thermal coefficient of expansion acts in a direction perpendicular to that of the first transparent substrate 42 so that the accumulated phase retardation of the optical wave associated with birefringence of the substrate is effectively cancelled. Metal contacts 46 are placed on either side of transmission window 41 of MQW 40. Contacts 46 are used to apply an electric field in the plane of the quantum well layers. A polarizer 48 is placed after transparent substrate 44 followed by a photodetector 50. Alternatively, a polarized beam splitter and pair of photodiodes may be used to detect the intensity of the polarized beams.

The present invention operates as follows. For a compressive (tensile) strain in the x-direction, the heavy-hole exciton absorption is increased (or decreased) for light polarized in that direction, while it is decreased (or increased) for light polarized perpendicular to that direction. This indicates that light polarized at 45 degrees with respect to the strain axis and tuned to the heavy-hole exciton absorption line will undergo a polarization rotation due to the anisotropy in the excitonic absorption. The polarizer 48 placed beneath transparent substrate 44 is oriented such that the transmitted light is blocked unless it is in polarity with the orientation of polarizer 48. Application of an electric field in the plane of MQW 40 leads to ionization of the excitons which produces an anisotropic bleaching and concomitant line broadening of the anisotropic excitonic absorption. This phenomenon results in a polarization rotation of the transmitted optical field such that light passes through the polarizer and is detected by photodetector 50.

A small DC field (approximately 10 kV/cm) is required to ensure that the change in transmission is linear with the applied terahertz electromagnetic wave 2 (i.e., dT/dE is about constant) with polarizer 48 oriented for minimum transmission in the presence of the terahertz field. Since the frequency of the terahertz field is more than two orders of magnitude less than that of the optical field, the terahertz radiation at any one instant appears to the optical wave as a small static field superimposed on the comparatively large DC field. Depending on the phase of the terahertz field, the anisotropy in the optical absorption along with its associated polarization rotation at a given instant will be either increased or decreased, thus causing light to pass through polarizer 48.

Figure 13:
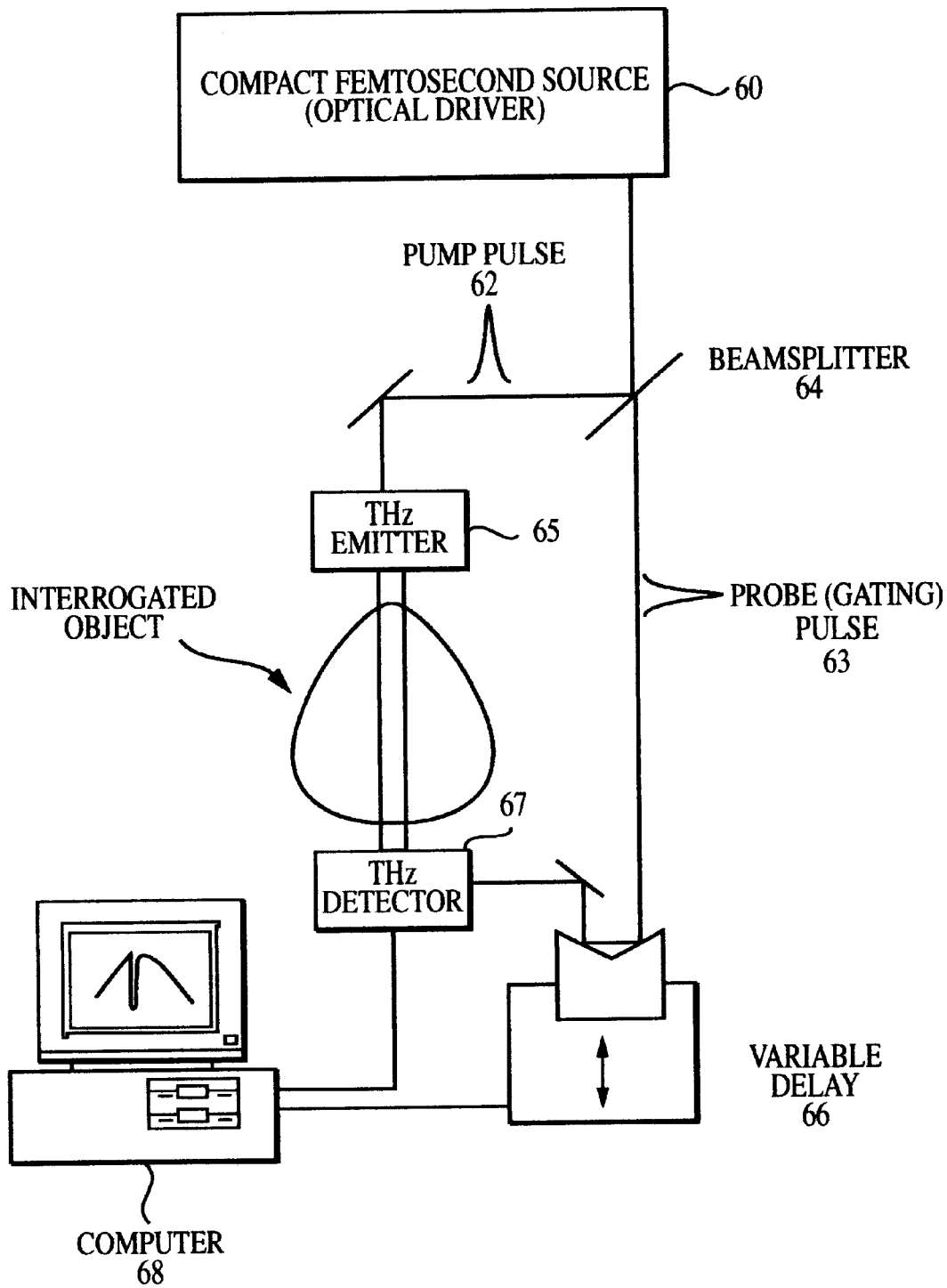
FIG. 13 shows a system for generation and detection of terahertz radiation.

In order for the detection to be coherent, the source of the terahertz radiation must be coherently linked to the detection system. FIG. 13 shows the details of how this may be accomplished. The optical driver 60 for the system is a compact diode-pumped laser producing pulses of approximately 100 fsec in duration. Alternatively, the optical driver 60 could be a fiber laser. A pulse is split into pump pulse 62 and probe or gating pulse 63 by beamsplitter 64. Pump pulse 62 is used to optically excite terahertz radiation from a terahertz emitter 65 (which may typically be a biased semiconductor producing terahertz radiation through optical rectification or by a photoconductive dipole antenna). The gating pulses pass through a variable optical delay line 66 that may be controlled by computer 68, before impinging on the terahertz detector 67. By varying the time delay between the pump pulse 62 and probe pulse 63 the probe pulse may be used to sample the terahertz waveform with approximately 100 fsec resolution, as a particular point on a terahertz waveform corresponds to a specific field, which leads to polarization rotation of the probe pulse for a given delay. The entire pulse waveform may be collected by scanning the probe pulse through the terahertz waveform.

In an alternative embodiment, a spectral filter such as a monochromator may be used after the polarizer to detect the rotation at the exciton peak, thus further increasing the sensitivity. Since the detection is background free, a photomultiplier may be used for photon counting to increase sensitivity. The polarizer may be replaced by a polarizer beamsplitting cube, which would split the transmitted beam into two parts with polarization dependent intensities. In the absence of the terahertz pulse, the intensities of the two beams could be subtracted using two photodetectors, so that a signal would only be present when there was polarization rotation due to the presence of terahertz radiation. The probe pulse on the terahertz detector may also be replaced by a CW laser tuned to the exciton peak, with the data encoded by the terahertz waveform recovered by upconversion in a nonlinear crystal using the probe pulse. This will be a sensitive means of detection because there are two background filters (the polarization and frequency conversion process), while avoiding any spectral deconvolution which may be necessary due to the exciton coherence time (a property that is material dependent when using a monochromator). It also makes the monochromator unnecessary. The delay line may be replaced by an oscillating retroreflector, which would permit the real time signal acquisition at audio frequencies suitable for spectral analysis via a digital signal processor.

Having thus shown and described what are at present considered to be preferred embodiments of the present invention, it should be noted that the same have been made by way of illustration and not limitation. Accordingly, all modifications, alterations and changes coming within the spirit and scope of the present invention are herein meant to be included.

We claim:

1. A light polarization sensitive detector of terahertz frequency electromagnetic radiation comprising:

a multiple quantum well and having a top and a bottom;

a first transparent substrate having a front side and a back side, the front side of the first transparent substrate bonded to the bottom of the multiple quantum well, and having an antsotropy in the thermal coefficient of expansion in a plane substantially perpendicular to the surface normal of the multiple quantum well;

a second transparent substrate substantially identical to the first transparent substrate positioned beneath the back side of the first transparent substrate and oriented such that an optical anisotropy of the first transparent substrate is offset by the second substrate;

metal contacts affixed to the top of the multiple quantum well; and wherein the first and second transparent substrates are comprised of LiTaO3.

2. A light polarization sensitive detector of terahertz frequency electromagnetic radiation according to claim 1 wherein the bond between the first transparent substrate and multiple quantum well is a high temperature thermal bond.

3. A light polarization sensitive detector of terahertz frequency electromagnetic radiation according to claim 2 wherein the high temperature bond is effected by using a UV-adhesive and a UV lamp.

* * * * *